United States Patent
Chen et al.

(10) Patent No.: US 11,958,796 B2
(45) Date of Patent: Apr. 16, 2024

(54) HYDROPHILIC AND PARTICULARLY WATER SOLUBLE DBOV-DERIVATIVES

(71) Applicant: Max-Planck-Gesellschaft zur Förderung der Wissenschaften e.V., Munich (DE)

(72) Inventors: Qiang Chen, Mainz (DE); Akimitsu Narita, Mainz (DE); Klaus Müllen, Cologne (DE); Sapun Parekh, Mainz (DE); Mischa Bonn, Frankfurt am Main (DE); Xiaomin Liu, Mainz (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 546 days.

(21) Appl. No.: 17/282,748

(22) PCT Filed: Sep. 30, 2019

(86) PCT No.: PCT/EP2019/076497
§ 371 (c)(1),
(2) Date: Apr. 2, 2021

(87) PCT Pub. No.: WO2020/070086
PCT Pub. Date: Apr. 9, 2020

(65) Prior Publication Data
US 2022/0009870 A1 Jan. 13, 2022

(30) Foreign Application Priority Data

Oct. 3, 2018 (EP) .................................... 18198506
Oct. 9, 2018 (EP) .................................... 18199447

(51) Int. Cl.
C07C 43/205 (2006.01)

(52) U.S. Cl.
CPC ................. C07C 43/2055 (2013.01)

(58) Field of Classification Search
None
See application file for complete search history.

(56) References Cited

PUBLICATIONS

G. M. Paternò, et al., Synthesis of Dibenzo[hi,st]ovalene and Its Amplified Spontaneous Emission in a Polystyrene Matrix, Angew. Chem. Int. Ed. 2017, 56, 6753. (Year: 2017).*
Paterno GM: "Synthesis of dibenzo[hi,st]ovalene and its amplified spontaneous emission in a polystyrene matrix", Angewandte Chemie Int. Ed., vol. 56, May 11, 2017, pp. 6753-6757.
Lemenager G et al. "Super-resolution fluorescence imaging of biocompatible carbon dots" NANOSCALE, vol. 6, Jun. 3, 2014, pp. 8617-8623.
Li et al: "Blinking silica nanoparticles for optical super resolution imaging of cancer cells", RSC Advances, vol. 7, Oct. 17, 2017, pp. 48738-48744.
He et al "High-density super-resolution localization imaging with blinking carbon dots", Anal. Chem. 2017, vol. 89, pp. 11831 to 11838.
Khan et al "Reversible photoswitching of carbon dots", Sci. Rep., 2015, vol. 5, 11423.
Verma et al. "Single-molecule analysis of fluorescent carbon dots towards localization-based super-resolution microscopy", Methods Appl. Fluoresc., 2016, vol. 4, 044006.
Muthurasu et al. "Facile and simultaneous synthesis of graphene quantum dots and reduced graphene oxide for bio-imaging and supercapacitor applications", New. J. Chem., 2016, vol. 40, pp. 9111 to 9124.
Sarkar et al "Graphene quantum dots from graphite by liquid exfoliation showing excitation-independent emission, fluorescence upconversion and delayed fluorescence", Phys. Chem. Chem. Phys., 2016, vol. 18, pp. 21278 to 21287.
Gan et al. "Mechanism for excitation-dependent photoluminescence from graphene quantum dots and other graphene oxide derivatives: consensus, debates and challenges", Nanoscale, 2016, vol. 8, pp. 7794 to 7807.
Thakur et al."Milk-derived multi-fluorescent graphene quantum dot-based cancer theranostic system", Mater. Sci. Eng. C, 2016, vol. 67, pp. 468 to 477.
Zheng et al "Glowing graphene quantum dots and carbon dots: Properties, syntheses, and biological applications", nSmall, 2015, vol. 11, pp. 1620 to 1636.
Sun et al. "Recent advances in graphene quantum dots for sensing", Mater. Today, 2013, vol. 16, pp. 433 to 442.

(Continued)

Primary Examiner — Joseph R Kosack
Assistant Examiner — Quincy A McKoy
(74) Attorney, Agent, or Firm — Hershkovitz & Associates, PLLC; Abe Hershkovitz; Eugene C. Rzucidio

(57) ABSTRACT

The present invention relates to a compound having the general formula (1) wherein in the general formula (1) the residues $R_1$ to $R_8$ and Ar are the same or different and are independently from each other selected from the group consisting of hydrogen, unsubstituted hydrocarbon groups, substituted hydrocarbon groups and inorganic groups, wherein at least one of the residues $R_1$ to $R_8$ and Ar is a hydrophilic group, such as for instance a group comprising one or more polyethylene groups.

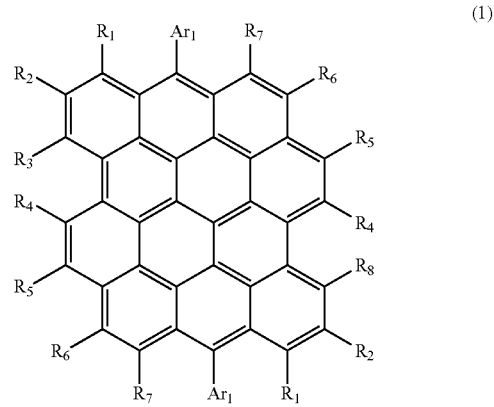

(1)

13 Claims, 3 Drawing Sheets

(56) References Cited

PUBLICATIONS

Yang et al. "Versatile application of fluorescent quantum dot labels in super-resolution fluorescence microscopy", *ACS Photonics*, 2016, vol. 3, pp. 1611 to 1618.
Zhao et al. "Single photon emission from graphene quantum dots at room temperature", *Nat. Commun.*, 2018, pp. 1 to 12.
International Search Report dated Nov. 12, 2019 in PCTIEP2019/076497.
International Preliminary Report on Patentabillity (IPRP) dated Apr. 15, 2021 in PCT/EP2019/076497.

* cited by examiner

HYDROPHILIC AND PARTICULARLY WATER SOLUBLE DBOV-DERIVATIVES

The present invention relates to hydrophilic and particularly water soluble derivatives of dibenzo[hi,st]ovalene (DBOV), which are in particularly suitable to be used in super-resolution microscopy.

Super-resolution microscopy denotes microscopy techniques, which have a higher resolution than the diffraction limit of light, i.e. which have a higher lateral resolution than $\lambda/(2\,N.A.)$, wherein N.A. is the numerical aperture and $\lambda$ is the wavelength of the light used. Prominent examples for super-resolution microscopy techniques are single-molecule localization microscopy (SMLM) and stimulated emission depletion microscopy (STED).

The SMLM techniques base on the use of fluorophores, i.e. fluorescent chemical compounds that emit light after having been excited by the absorption of radiation, as markers, which have a low duty cycle. Fluorophores with a low duty cycle are characterized in that—when radiated with excitation radiation—the ratio of the period of time during which they are in the "on" state (i.e. radiation emitting state) divided by the period of time during which they are in the "off" state (i.e. non-emissive ground state or "dark state", respectively) is low. In other words, the used fluorophores show—seen over the time—a fluorescence emission spectrum with emission peaks having a short peak width on the time axis, wherein the time interval between two emission peaks is comparable long. A fluorophore having a low duty cycle is also denoted to have good blinking properties. Therefore, when a sample of which parts are labelled with the respective fluorophore molecules is excited by a laser, such as when a cell of which the microtubules are labelled with the respective fluorophore molecules is excited by a laser, at every point of time only a comparable small number of the fluorophore molecules is in the "on" state and emits fluorescence radiation for a comparable short time period. Thus, the probability that adjacent fluorophore molecules emit radiation at the same point of time is quite low so that consequently the risk of an overlap of the emission signals of two adjacent fluorophore molecules is very low. On account of this reason, a spatial and temporal separation of the fluorescence emission profiles of the single fluorophore molecules is obtained, which allows to precisely reconstruct the position of single fluorophores by mapping the (usually many thousands) pictures obtained over the measurement time.

Apart from good blinking properties, fluorophores suitable for SMLM shall provide further properties. In order to be useable for bio-imaging application, such as for the microscopy of a biological system, such as a cell, it is important that the fluorophore has a good water solubility. Moreover, it is important is particularly that the fluorophore has a high photon number, i.e. that it emits a high number of photons during its short "on" states. Furthermore, it is preferred that the fluorophore has a very high photostability so that it can be cycled between the "on" state and "off" state as often as possible and thus does not photobleach within short term, i.e. does loose its ability to be excited into the "on" state after a low number of cycles between the "on" state and "off" state. Apart from that, the fluorophore shall have a small size of below 5 nm and ideally of below 1 nm (in order to allow an excellent spatial resolution), a comparable narrow excitation spectrum, a comparable narrow emission spectrum and shall emit visible light, in order to allow to obtain an excellent spatial separation of the fluorescence emission profiles of the single fluorophore molecules. Particularly preferably, the fluorophore shall have a low toxicity.

Organic dyes, such as Alexa Fluor® 647 dye distributed from ThermoFisher Scientific, show good blinking properties, a narrow excitation spectrum as well as a narrow emission spectrum. However, a special buffer is needed, such as an oxygen-depleted environment in combination with redox agents, in order to maintain these properties. This makes the process not only laborious, but makes it in particular challenging to perform a high-quality imaging in all environments. Moreover, such dyes have good blinking behaviours only within several hours, such as e.g. less than 8 hours, since the special buffer condition changes over time.

Also known for the purpose of being used as fluorophore for SMLM are so called carbon dots (CDs), which are supposed to be composed of more or less spherical-shaped amorphous carbon. CDs are normally synthesized from carbon soot or carbon black. This is a so-called "top-down" method, i.e. a method, in which a comparable large structure, namely carbon soot or carbon black, is disintegrated into a smaller structure, namely CDs. For instance, carbon black is refluxed with nitric acid for 24 hours, before the resultant suspension is cooled to room temperature and then centrifuged. After discard of the pellet, the supernatant is heated and dried. The so obtained solid is resuspended in water and ultrafiltrated. Carbon dots as well as their preparation methods are disclosed e.g. by Lemenager et al., "Super-resolution fluorescence imaging of biocompatible carbon dots", Nanoscale, 2014, volume 6, pages 8617 to 8623, by He et al., "High-density super-resolution localization imaging with blinking carbon dots", Anal. Chem. 2017, volume 89, pages 11831 to 11838, by Khan et al., "reversible photoswitching of carbon dots", Sci. Rep., 2015, volume 5, 11423, and by Verma et al., "Single-molecule analysis of fluorescent carbon dots towards localization-based super-resolution microscopy", Methods Appl. Fluoresc., 2016, volume 4, 044006. However, the CDs as are quite large having dimensions of at least 3 nm up to 60 nm and thus too large to obtain a very good resolution with SMLM. Moreover, due to the "top-down" production method, CDs are a mixture of a variety of differently oxidized molecules, which are only sorted according to their size by different membranes. On account of this reason CDs are heterogeneous both in size and structure and they are oxidized to variable extents. Thus, CDs do not behave like material being composed of one specific type of molecule. On account of their different species and their heterogeneity in size, the emission spectra and in particular the excitation spectra of CDs are quite broad. In addition, their water solubility is too low for being appropriately used in bio-imaging applications. Furthermore, due to their undefined chemical structure they cannot be used in targeted intracellular delivery and for specific labelling of subcellular targets.

Compositions being similar to CDs are graphene quantum dots (GQDs). GQDs should be monolayer nanographene by definition, but are often stacked multilayer graphite mixtures containing structures and bear many different oxygen-based functional groups, which derive from their synthesis. Likewise to CDs, GQDs are normally synthesized from carbon soot or carbon black by a "top-down" method. GQDs as well as their preparation methods are disclosed e.g. by Muthurasu et al., "Facile and simultaneous synthesis of graphene quantum dots and reduced graphene oxide for bio-imaging and supercapacitor applications", New. J. Chem., 2016, volume 40, pages 9111 to 9124, by Sarkar et al., "Graphene quantum dots from graphite by liquid exfoliation showing excitation-independent emission, fluorescence upconversion and delayed fluorescence", Phys. Chem. Chem. Phys., 2016, volume 18, pages 21278 to 21287, and by Gan et al., "Mechanism for excitation-dependent photoluminescence from graphene quantum dots and other graphene oxide derivatives: consensus, debates and challenges", Nanoscale, 2016, volume 8, pages 7794 to 7807. On account of being mixtures of single species being heterogeneous both in size and structure, the emission spectra as well as in particular their excitation spectra are quite broad. In particular GQDs have a low quantum yield and the broadened excitation spectrum reaches into the emission spectrum. In addition, they do not have a sufficient water solubility for being appropriately used in bio-imaging applications. Moreover, it is described in the prior art that GQDs have no blinking properties, i.e. are not suitable for SMLM, such as by Thakur et al., "Milk-derived multi-fluorescent graphene quantum dot-based cancer theranostic system," Mater. Sci. Eng. C, 2016, volume 67, pages 468 to 477, by Zheng et al., "Glowing graphene quantum dots and carbon dots: Properties, syntheses, and biological applications," Small, 2015, volume 11, pages 1620 to 1636, by Sun et al, "Recent advances in graphene quantum dots for sensing," Mater. Today, 2013, volume 16, pages 433 to 442, and by Zhao et al, "Single photon emission from graphene quantum dots at room temperature," Nat. Commun., 2018, pages 1 to 12.

Semiconductor quantum dots, such as ZnS-coated CdSe-QDs, as they are disclosed by Yang et al., "Versatile application of fluorescent quantum dot labels in super-resolution fluorescence microscopy", ACS Photonics, 2016, volume 3, pages 1611 to 1618, have comparable bad blinking properties and have a comparable broad excitation spectrum in the UV range. In addition, they are toxic. Thus, they are not suitable for performing high quality SMLM.

STED is a microscopy technique, which uses two laser beams of different wavelength. While the first laser beam is focused into the sample and excites the fluorophores contained therein so that they emit fluorescence radiation at a higher wavelength than the excitation wavelength, the second laser beam, which is called STED laser, is irradiated in form of a circular ring concentrically around the first laser beam so as to quench fluorescence in the outer peripheral area of the first laser beam. On account of this, fluorescence can only emit from the central region of a fluorophore into which the first laser beam irradiates so that the area of the sample which actually emits fluorescence is significantly smaller than the area, which is irradiated with the first excitation laser. Thus, a very sharp fluorescence emission is obtained for each fluorophore. In order to obtain a complete picture of the sample, the sample is scanned by the two lasers point for point. An important requirement for fluorophores used in STED microscopy is that they have comparable narrow excitation and emission spectra. However, as set out above the known CDs and GQDs have—on account of being mixtures with a high structural heterogeneity—comparable broad excitation and emission spectra and particularly the broad excitation spectra of GQDs reach deeply into the emission spectra. On account of this reason, both, CDs as well as GQDs limit the choice for the STED wavelength and also induce a lot of background noise. In addition, the known organic dyes are not satisfying for STED microscopy due to their comparable bad photostability leading to photobleaching after two to three hours.

Accordingly, the object underlying the present invention is to provide a compound, which is well suitable for being used in high-resolution microscopy techniques and which has a good water solubility as that it can be appropriately used in bio-imaging applications, such as for the microscopy of biological systems, such as of cells. Preferably, the compound has furthermore good blinking properties and is characterized by a high photon number, a very high photostability, a low toxicity, a small size of below 1 nm, a comparable narrow excitation spectrum and a comparable narrow emission spectrum.

In accordance with the present invention, this object is satisfied by providing a compound having the general formula (1):

general formula (1)

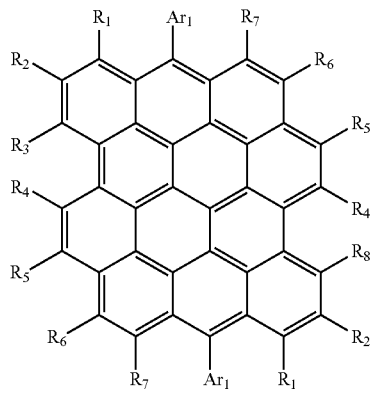

wherein in the general formula (1) the residues $R_1$ to $R_8$ and Ar are the same or different and are independently from each other selected from the group consisting of hydrogen, unsubstituted hydrocarbon groups, substituted hydrocarbon groups and inorganic residues, wherein at least one of the residues $R_1$ to $R_8$ and Ar is a hydrophilic group.

This solution bases on the surprising finding that such DBOV derivatives do not only have a good water solubility, but also have all the properties being necessary for being used in high-resolution microscopy, such as in STED and SMLM. More specifically, the respective compounds have excellent blinking properties which are environment-independent, a high photon number, a very high photostability, a low toxicity, a small size of below 1 nm, a comparable narrow excitation spectrum and a comparable narrow emission spectrum. More specifically, the photon number is about 5,000 to 10,000 and the duty cycle is as low as about 0.001. These compounds are further characterized by a quantum yield of about 0.80 and by an extinction coefficient of about 70,000 $M^{-1}$ $cm^{-1}$. A particular further advantage in comparison to CDs and GQDs is that the respective compounds may be synthesized with a "bottom-up" method from smaller molecules so that compounds being homogenous both in size and structure are obtained, and not, like CDs and GQDs, a mixture of different species. This is a decisive reason why the excitation spectra as well as the emission spectra of these compounds are comparable narrow. A particular advantage of the compounds having the general formula (1) is that their water solubility may be easily tailored to a desired value by appropriately selecting the kind of hydrophilic group and the number of hydrophilic groups per molecule.

The terms group, residue and moiety are used in the present invention with the same meaning, wherein each of these terms denote in the sense of the present invention a part of a molecule, wherein the group, residue or moiety, respectively may comprise one atom or two or more atoms bound to each other. If it is mentioned that a group comprises one or more moieties, then the term moiety is intended to denote a part of the group, which in turn denotes a part of the whole molecule, but which is in fact still a group. Thus, in fact the terms group, residue and moiety are in the present invention interchangeable. Thus, any of the below described moieties is in fact a group and any of the below described groups is in fact a group so that for instance if below an alkylene moiety is mentioned it is in fact an alkylene group.

A hydrophilic group means in accordance with the present invention a group, which enhances the solubility of this molecule in water, like hydroxy groups, carboxyl groups, amino groups, sulfhydryl groups; ether, ester, phosphodiester, glycosidic linkages; peptide bonds or the like.

In the general formula (1) both residues $R_1$ may be the same, both residues $R_2$ may be the same, both residues $R_3$ may be the same, both residues $R_4$ may be the same, both residues $R_5$ may be the same, both residues $R_6$ may be the same and both residues $R_7$ may be the same, whereas residues $R_1$ may be the same or different to the other residues, residues $R_2$ may be the same or different to the other residues and so forth. It is actually preferred that both residues $R_1$ are the same, both residues $R_2$ are the same, both residues $R_3$ are the same and so forth, but the present invention is not limited thereto. Thus, both residues $R_1$ may be different to each other, both residues $R_2$ may be different to each other and so forth.

In principle, the present invention is not particularly limited concerning the nature of the at least one hydrophilic group. The more hydrophilicity or solubility in water, respectively, is desired, the more hydrophilic groups and/or stronger hydrophilic groups have to be used.

Suitable examples for hydrophilic groups to be used in the present invention are anionic groups, cationic groups and non-charged hydrophilic groups. Thus, in accordance with an embodiment of the present invention, at least one of the residues $R_1$ to $R_8$ and Ar in the general formula (1) is a hydrophilic group, which is selected from the group consisting of anionic groups, cationic groups and non-charged hydrophilic groups comprising one or more moieties selected from inorganic acid moieties, organic acid moieties, ester moieties, amide moieties, hydroxy moieties, thiol moieties, amino moieties, aldehyde moieties, ketone moieties, acryl moieties, ether moieties, thioether moieties, sulfhydryl moieties, glycosidic linkages, peptide bonds and arbitrary combinations thereof.

More preferably, at least one of the residues $R_1$ to $R_8$ and Ar of the general formula (1) is a hydrophilic group, which consists of or comprises one or more moieties being selected from the group consisting of quaternary amino moieties, iminium salt moieties, pyrrolidinium salt moieties, pyrrolium salt moieties, pyrazolidinum salt moieties, pyrazolidinum salt moieties, imidazolium salt moieties, imidazolidinum salt moieties, piperidinium salt moieties, pyridinium salt moieties, piperazinium salt moieties, morpholinium salt moieties, thiomorpholinium salt moieties, oxazine salt moieties, thiazine salt moieties, indolinium salt moieties, indole salt moieties, sulfate moieties, phosphate moieties, nitrate moieties, sulfonate moieties, carboxylic acid moieties, sulfonic acid moieties, sulfenic acid moieties, sulfinic acid moieties, phosphonic acid moieties, phosphenic acid moieties, phosphinic acid moieties, sugar moieties, ester moieties, amide moieties, hydroxy moieties, thiol moieties, amino moieties, aldehyde moieties, ketone moieties, acryl moieties, ether moieties, thioether moieties, triazol residues and arbitrary combinations thereof.

Particular good results are obtained, when at least one of the residues $R_1$ to $R_8$ and Ar of the general formula (1) is a hydrophilic group, which consists of or comprises one or more moieties being selected from the group consisting of quaternary amino moieties, iminium salt moieties, pyridinium salt moieties, sulfate salt moieties, sulfonate moieties, carboxylic acid moieties, sulfonic acid moieties, ester moieties, amide moieties, ether moieties, triazol residues and arbitrary combinations thereof.

Exemplarily, at least one of the residues $R_1$ to $R_8$ and Ar in the general formula (1) is a hydrophilic group according to one of the below formulae:

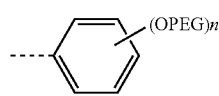 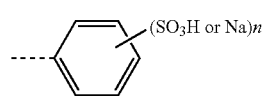 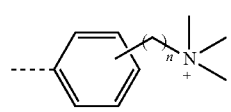 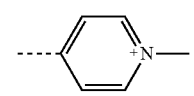

n = 1-5    n = 1-5    n = 1-5

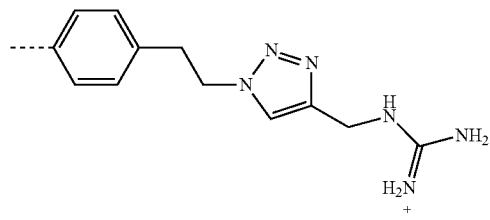 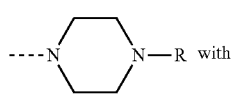 R = 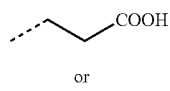

or

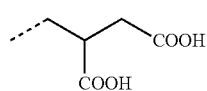

-continued
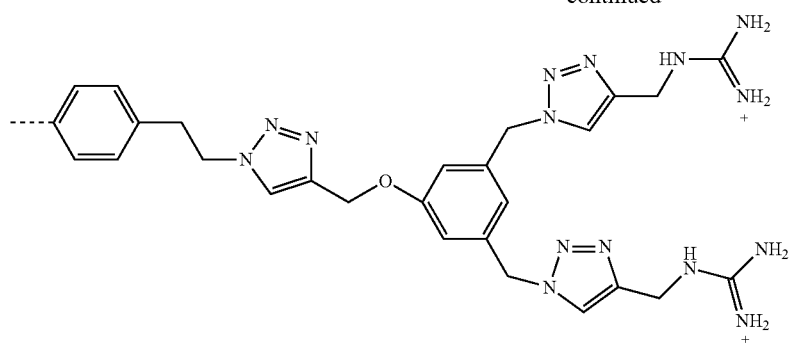
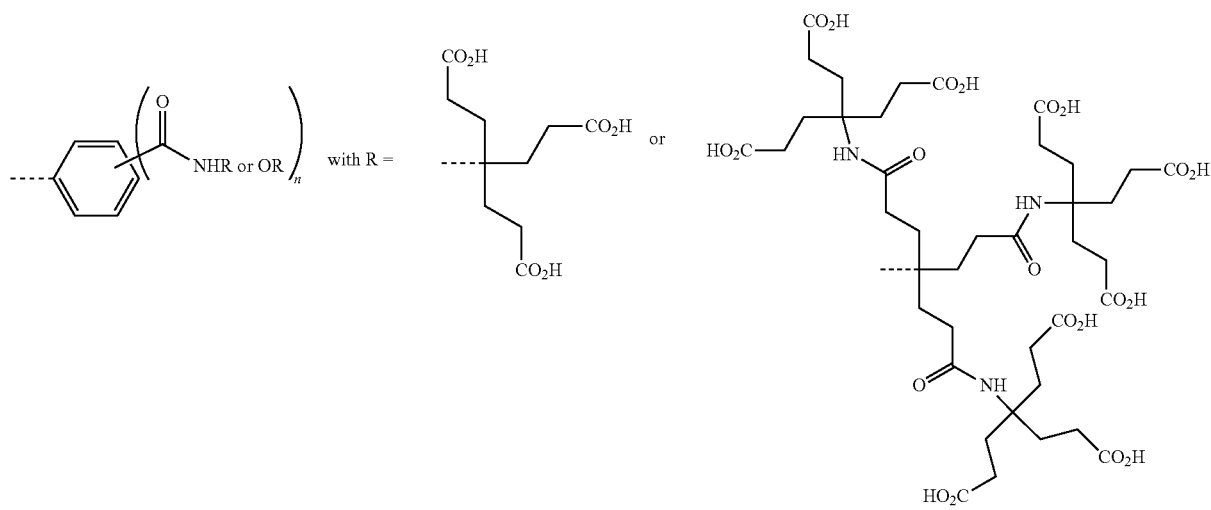
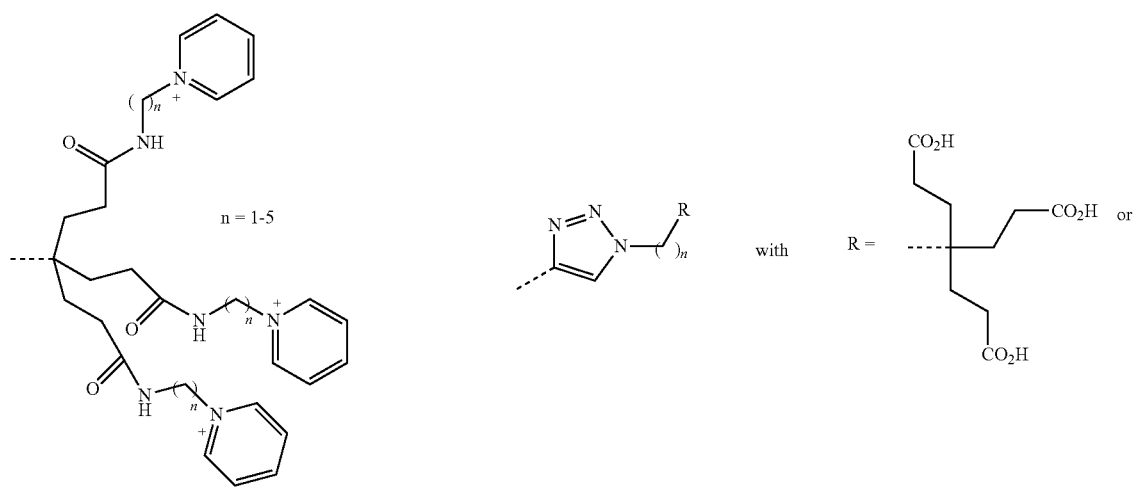

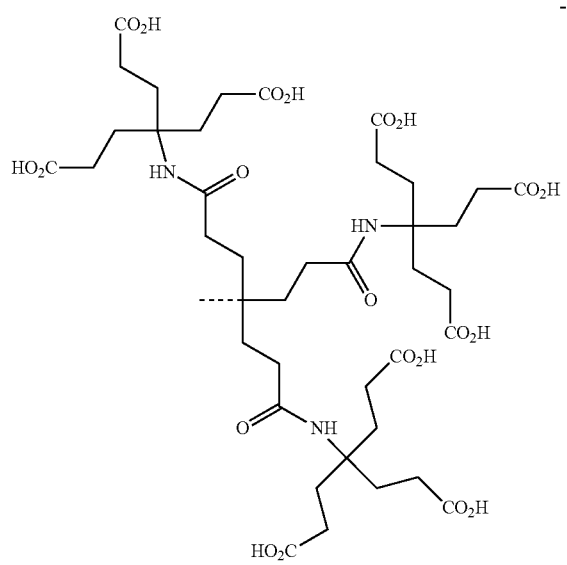
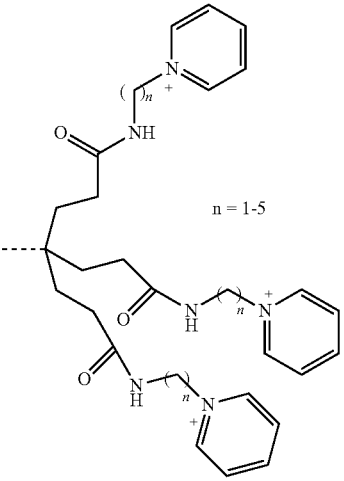

In accordance with a particular preferred embodiment of the present invention, at least one of the residues $R_1$ to $R_8$ and Ar of the general formula (1) is a hydrophilic group, which is a polyalkylene glycol group and preferably is a group comprising one to five and preferably two to four polyalkylene glycol moieties. Such polyalkylene glycol groups are not only highly hydrophilic, but have in addition the advantage of being easily bondable to a huge variety of molecules so that the respective DBOV derivatives including polyalkylene glycol groups can be easily synthesized. Furthermore, by appropriately adjusting the number of polyalkylene glycol moieties, the kind of the alkylene moieties and the length of the single polyalkylene glycol moieties, the hydrophilicity of the DBOV derivative may be easily tailored to a desired value.

Good results are in particular obtained, when each of the polyalkylene glycol moieties has a repeating number of 2 to 20, i.e. each polyalkylene glycol moiety comprises 2 to 20 alkoxy moieties, i.e. alkylene moieties being connected with each other by means of an oxygen atom into a linear chain. Particularly preferred as hydrophilic group is a group which comprises one to five and preferably two to four polyalkylene glycol moieties with each having a repeating number of 2 to 20, such as a glycol phenyl group being mono-substituted with polyalkylene, a phenyl group being di-substituted with polyalkylene or a phenyl group being tri-substituted with polyalkylene.

Examples for preferred polyalkylene glycol moieties are polypropylene moieties and particularly polyethylene moieties having a repeating number of 2 to 20.

Thus, a more preferred hydrophilic group of the present invention is a phenyl group, which is substituted with two to five polyalkylene glycol moieties, preferably with two to five polyethylene glycol moieties and more preferably with two to five tetraethylene glycol moieties, pentaethylene glycol moieties or hexaethylene glycol moieties. Specific examples therefore are phenyl groups, which are substituted with two to five dioxa-$C_{7-10}$-alkyl moieties, namely dioxaheptyl moieties, dioxaoctyl moieties, dioxanonyl moieties and dioxadecyl moieties, trioxa-$C_{10-13}$-alkyl moieties, namely trioxadecyl moieties, trioxaundecyl moieties, trioxadodecyl moieties and trioxatridecyl moieties, as well as tetraoxa-$C_{12-14}$-alkyl moieties, namely tetraoxadodecyl moieties, tetraoxatridecyl moieties and tetraoxatetradodecyl moieties. A particular preferred example is a phenyl group being substituted with three trioxatridecyl moieties, such as a 3,4,5-tris(2,5,8,11-tetraoxatridecan-13-yloxy)phenyl group.

Other examples for hydrophilic groups are 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl.

In accordance with an equally preferred embodiment of the present invention, at least one of the residues $R_1$ to $R_8$ and Ar of the general formula (1) is a hydrophilic group, which consists of or comprises one or more sulfonate moieties, one or more quaternary ammonium moieties, one or more amide moieties, one or more imine moieties and/or one or more pyridinium moieties.

In a further development of the idea of the present invention, at least two of the residues $R_1$ to $R_8$ and Ar of the general formula (1) are a hydrophilic group and preferably at least residues $R_3$ and $R_8$ are a hydrophilic group, wherein the hydrophilic groups of the at least two residues may be the same or different to each other.

As set out above, the hydrophilicity or solubility in water, respectively, of the compound having the general formula (1) may be tailored to the desired value by appropriately adjusting the number of hydrophilic groups and the kind of the hydrophilic groups.

In accordance with a further particularly preferred embodiment of the present invention, the compound having the general formula (1) has a solubility in water at 23° C. of at least 0.01 g/l, preferably of at least 0.05 g/l and more preferably of at least 0.1 g/l.

In accordance with the present invention, the solubility of the compound having the general formula (1) in water at 23° C. is measured as follows: 1.0 mg sample is weighed into an Erlenmeyer flask and is then mixed homogeneously with 4 ml of water with a spatula at 23° C. The remaining substance on the spatula is stripped off with a magnetic stirrer bar, which is then added to the Erlenmeyer flask. While stirring with a magnetic stirrer, water is added dropwise with a burette until the solution in the Erlenmeyer flask becomes clear at 23° C. After that, the solubility of compound in water is calculated by calculating the ratio of weighed compound divided by the volume of added water and then by recalculating this ratio to 1 l of water.

Those residues $R_1$ to $R_8$ and Ar of the general formula (1), which are not an aforementioned hydrophilic group, may be the same or different and may be independently from each other selected from the group consisting of hydrogen, unsubstituted alkyl groups, substituted alkyl groups, unsubstituted alkenyl groups, substituted alkenyl groups, unsubstituted alkynyl groups, substituted alkynyl groups, unsubstituted alkoxy groups, substituted alkoxy groups, unsubstituted cycloalkyl groups, substituted cycloalkyl groups, unsubstituted aryl groups, substituted aryl groups, unsubstituted aralkyl groups, substituted aralkyl groups, unsubstituted hetaryl groups, substituted hetaryl groups, azide groups, and groups formed in that two of adjacent residues of $R_1$ to $R_8$ and Ar are linked with each other to form an aromatic, heteroaromatic, cyclic or heterocyclic group.

Preferably, those residues $R_1$ to $R_8$ and Ar of the general formula (1), which are not an aforementioned hydrophilic group, may be the same or different to each other and are independently from each other selected from the group consisting of hydrogen; unsubstituted linear or branched $C_{1-30}$-alkyl groups; substituted linear or branched $C_{1-30}$-alkyl groups whose hydrocarbon chain is interrupted by one or more —O—, —S—, —NR'— with R' being $C_{1-30}$-alkyl, $C_{1-30}$-alkenyl, $C_{1-30}$-alkynyl, $C_{1-30}$-alkoxy, $C_{6-20}$-aryl, $C_{6-20}$-heteroaryl, —CO— and/or —SO— groups; linear or branched $C_{1-30}$-alkyl groups whose hydrocarbon chain is monosubstituted or polysubstituted with a carboxyl group, a sulfo group, a hydroxy group, a cyano group, a C—C-alkoxy group and/or with a 5- to 7-membered heterocyclic group which is bonded via a nitrogen atom to the hydrocarbon chain; trialkylsilyl alkynyl groups; unsubstituted $C_{3-30}$-cycloalkyl groups; substituted $C_{1-30}$-cycloalkyl groups whose hydrocarbon chain is interrupted by one or more —O—, —S—, —NR'— with R' being $C_{1-30}$-alkyl, $C_{1-30}$-alkenyl, $C_{1-30}$-alkynyl, $C_{1-30}$-alkoxy, $C_{6-20}$-aryl, $C_{6-20}$-heteroaryl, —CO— and/or —SO— groups; linear or branched $C_{1-30}$-cycloalkyl groups whose hydrocarbon chain is monosubstituted or polysubstituted with a carboxyl group, a sulfo group, a hydroxy group, a cyano group, a C—C-alkoxy group and/or with a 5- to 7-membered heterocyclic group which is bonded via a nitrogen atom to the hydrocarbon chain; phenyl groups; naphthyl groups; anthryl groups; pyrenyl groups; phenyl-, naphthyl-, anthryl- or pyrenyl-groups being monosubstituted or polysubstituted with $C_{1-18}$-alkyl, $C_{1-18}$-alkoxy, halogen, hydroxy, cyano, carboxyl, —CONHR with R being $C_{1-30}$-alkyl, $C_{1-30}$-alkenyl, $C_{1-30}$-alkynyl, $C_{1-30}$-alkoxy, $C_{6-20}$-aryl or $C_{6-20}$-heteroaryl, —NHCOR with R being $C_{1-30}$-alkyl, $C_{1-30}$-alkenyl, $C_{1-30}$-alkynyl, $C_{1-30}$-alkoxy, $C_{6-20}$-aryl, $C_{6-20}$-heteroaryl; azide groups and groups formed in that two of adjacent residues of $R_1$ to $R_8$ and Ar are linked with each other to form an aromatic, heteroaromatic, cyclic or heterocyclic group.

It is also preferred, if those residues $R_1$ to $R_8$ and Ar of the general formula (1), which are not an aforementioned hydrophilic group, are the same or different to each other and are independently from each other selected from the group consisting of hydrogen, unsubstituted linear or branched $C_{1-30}$-alkyl groups, unsubstituted $C_{3-30}$-cycloalkyl groups, phenyl groups, naphthyl groups, anthryl groups, pyrenyl groups, azide groups, polyethylene groups with 2 to 20 ethylene moieties, phenyl ethylene, triisopropylsilyl ethynyl, trimethylsilyl ethynyl, and groups formed in that two of adjacent residues of $R_1$ to $R_8$ and Ar are linked with each other to form an aromatic, heteroaromatic, cyclic or heterocyclic group.

More preferably, those residues $R_1$ to $R_8$ and Ar of the general formula (1), which are not an aforementioned hydrophilic group, are the same or different to each other and are independently from each other hydrogen, a $C_{1-20}$-alkyl group, a $C_{1-20}$-alkenyl group, a $C_{1-20}$-alkynyl group, a $C_{4-20}$-cycloalkyl group, a $C_{5-20}$-aromatic group, a $C_{4-20}$-cycloaliphatic group or a $C_{5-20}$-heterocyclic group and two of adjacent residues of $R_1$ to $R_8$ and Ar may be linked with each other to form $C_{5-20}$-aromatic group, a $C_{4-20}$-cycloaliphatic group or a $C_{5-20}$-heterocyclic group.

Specific examples for those residues $R_1$ to $R_8$ and Ar of the general formula (1), which are not an aforementioned hydrophilic group, are:

Hydrogen, methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above names isooctyl, isononyl, isodecyl and isotridecyl are trivial names and originate from the alcohols obtained by the oxo synthesis); 2-methylthioethyl, 2-ethylthioethyl 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl; 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2 and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl; propan-2-on-1-yl, butan-3-on-1-yl, butan-3-on-2-yl and 2-ethylpentan-3-on-1-yl; 2-methylsulfonylethyl, 2-ethylsulfonylethyl 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butyl sulfonyl butyl; carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl; 2-hydroxyethyl, 3-hydroxypropyl, 1-hydroxyprop-2-yl 2- and 4-hydroxybutyl, 1-hydroxybut-2-yl and 8-hydroxy-4-oxaoctyl; cyanomethyl 2-cyanoethyl, 3-cyanopropyl, 2-methyl-3-ethyl-3-cyanopropyl, 7-cyano-7-ethylheptyl and 4,7-dimethyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy; carbamoyl, methylaminocarbonyl, ethyl aminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl; formylamino, acetylamino, propionylamino and benzoylamino; chlorine, bromine and iodine; phenylazo, 2-naphthylazo, 2-pyridylazo and 2-pyrimidylazo; phenyl, 2-naphthyl, 2- and 3-pyrryl, 2-, 3- and 4-pyridyl, 2-,4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl; 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl and 2,4,6-tri-sec-butylphenyl, 2-, 3- and 4-tert-butylphenyl, 2,4-, 2,5-, 3,5- and 2,6-di-tert-butylphenyl, 2,4,6-tri-tertbutylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, and 2,4-, 2,5-, 3,5- and 2,6-dichlorophenyl; 2-, 3- and 4-hydroxyphenyl and 2,4-, 2,5-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl, 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl, 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl; 4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl; cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4 and 5-ethylcyclooctyl, 3-, 4- and 5-propylcyclooctyl, 2- dioxanyl, 4-morpholinyl, 2- and 3-tetrahydrofuryl, 1-, 2- and 3-pyrrolidinyl and 1-, 2-, 3- and 4-piperidyl; phenylazide, 2-naphthylazide, 2-pyridylazd; alkynyl groups, e.g., ethynyl, propynyl, butynyl, pentynyl, hexynyl, heptynyl, octynyl, nonynyl, decynyl.

Particularly preferably, the residue $R_1$ in the general formula (1) is hydrogen or a $C_{1-20}$-alkyl group, residues $R_3$ and $R_8$ are a hydrophilic group, residues $R_2$ and $R_4$ to $R_7$ are hydrogen and residue Ar is aryl, a $C_{6-15}$-alkyl group or a trialkylsilyl alkynyl group.

In any of the aforementioned embodiments, the residue Ar of the general formula (1) is preferably selected from the group consisting of phenyl, trifluorphenyl, 1,5-dimethylphenyl, mesitylene, triisopropylsilyl ethynyl, trimethylsilyl ethynyl, phenylsilyl ethynyl and $C_{6-15}$-alkyl groups.

In accordance with another particularly preferred embodiment of the present invention, in the general formula (1) either: i) residue $R_1$ is a $C_{1-20}$-alkyl group, residues $R_3$ and $R_8$ are a hydrophilic group and preferably a polyalkylene glycol group and residues $R_2$ and $R_4$ to $R_7$ are hydrogen, or ii) residues $R_3$ and $R_8$ are a hydrophilic group and preferably a polyalkylene glycol group and residues $R_1$, $R_2$ and $R_4$ to $R_7$ are hydrogen, wherein Ar is as described above or also a hydrophilic group. Ar may be in these embodiments in particular phenyl, mesitylene, triisopropylsilyl ethynyl and trimethylsilyl ethynyl.

In accordance with a further embodiment of the present invention, in the general formula (1) at least two adjacent of the residues Ar and $R_1$ to $R_4$ are linked with each other to form an aromatic, heteroaromatic, cyclic or heterocyclic group. Exemplarily, the residues $R_3$ and $R_4$ and/or the residues $R_4$ and $R_8$ may be linked with each other to form an aromatic, heteroaromatic, cyclic or heterocyclic group. Preferably, the residues $R_3$ and $R_4$ and/or the residues $R_4$ and $R_8$ are linked with each other in this embodiment to form a heterocyclic group, such as in particular a heterocyclic imide group, more preferably a $C_{1-12}$—N-alkyl imide group and most preferably a N-hexyl imide group.

Likewise to this, in the general formula (1) the adjacent residues $R_3$ and $R_4$ and/or the adjacent residues $R_4$ and $R_8$ may be linked with each other to form a fumaric acid imide group, preferably a $C_{1-12}$—N-alkyl fumaric acid imide group and more preferably a N-hexyl fumaric acid imide group. In this embodiment it is preferred that residue $R_1$ is hydrogen or a $C_{1-20}$-alkyl group, two to four of the residues $R_2$ and $R_5$ to $R_7$ are a hydrophilic group, residue Ar is hydrogen, aryl or a trialkylsilyl alkynyl group and the remaining of residues $R_2$ and $R_5$ to $R_7$ are hydrogen.

Two examples for compounds in accordance with this embodiment are:

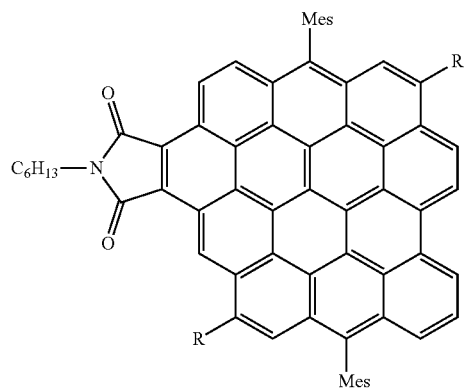

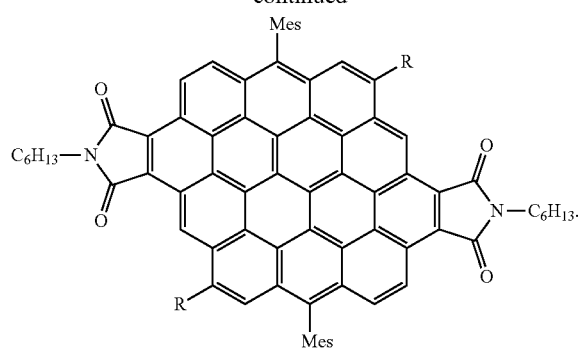

In a further development of the idea of the present invention it is proposed that at least one of residues $R_1$ to $R_8$ and Ar and preferably exactly one of the residues $R_1$ to $R_8$ and Ar of the general formula (1) is a group, which easily reacts with a respective coupling group at a target molecule, such as at a biomolecule, such as at a protein which shall be coupled with the compound of the general formula (1) in order to prepare a sample for high-resolution microscopy. For instance, any of one or more of the residues $R_1$ to $R_8$ and Ar of the general formula (1) may be a group with a terminal alkyne group. Such groups can be easily reacted for instance with an azide group of the target molecule, wherein the alkyne group and the azide group react under formation of a triazole group, which connects the fluorophore to the target molecule. Preferably, one of the residues $R_1$ to $R_8$ and Ar of the compound having the general formula (1) is a residue with a terminal alkyne group, such as a residue (e.g. a phenyl group) with a terminal ethyne group. Other examples for (clickable functional) groups, which easily react with a respective coupling group at a target molecule, are strained alkyne groups, strained alkene groups, azide groups, tetrazine groups, maleic imide groups. Specific examples for such (clickable functional) groups are:

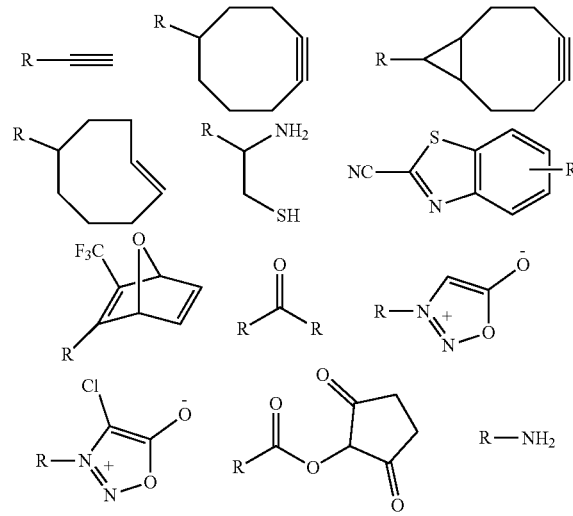

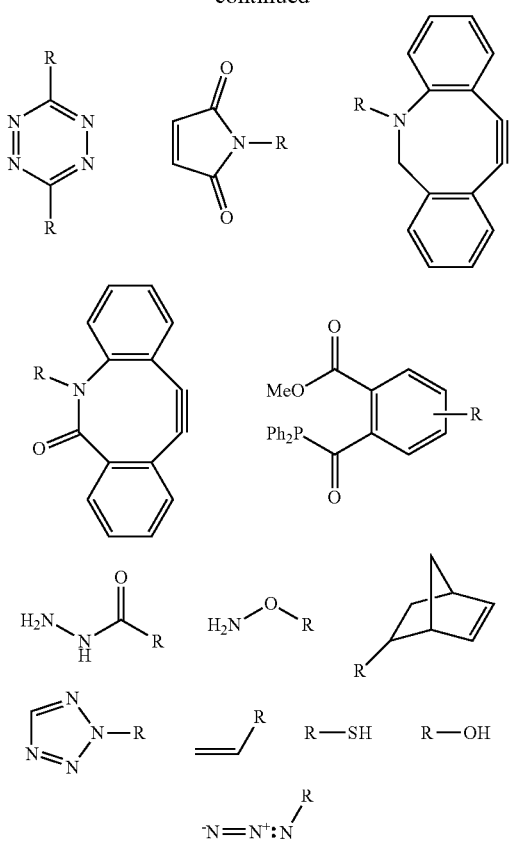

Particular preferred compounds in accordance with the present invention are:

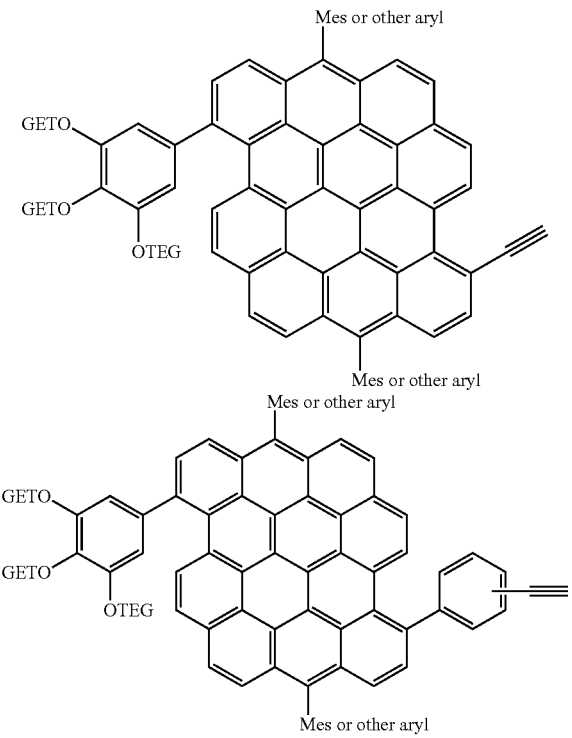

17
-continued

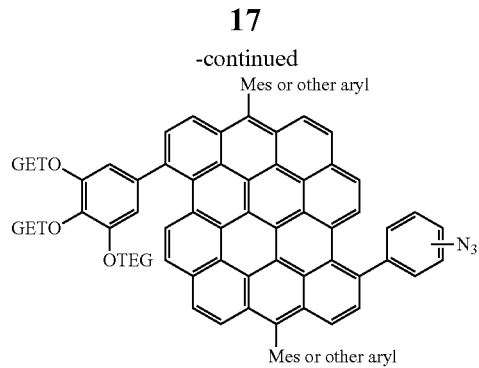

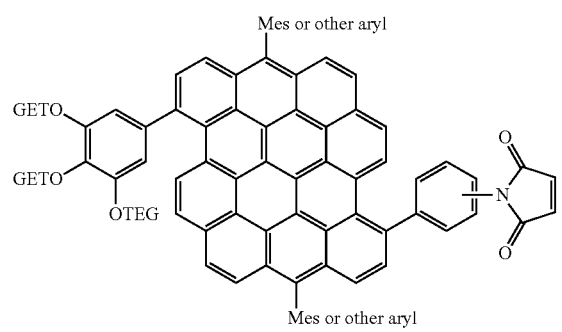

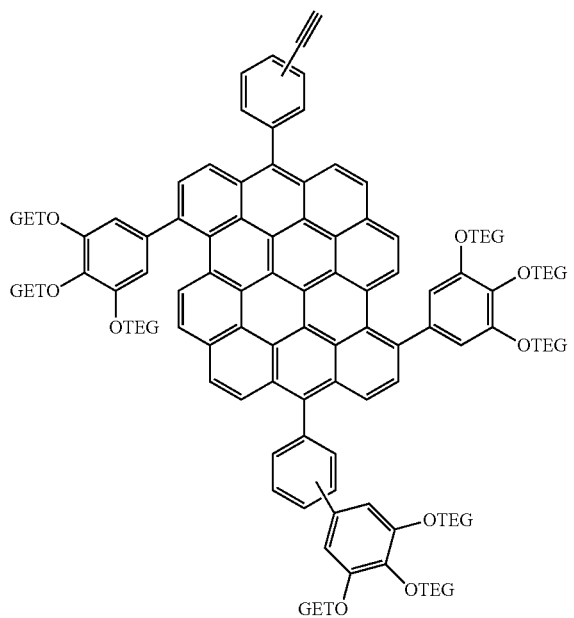

18
-continued

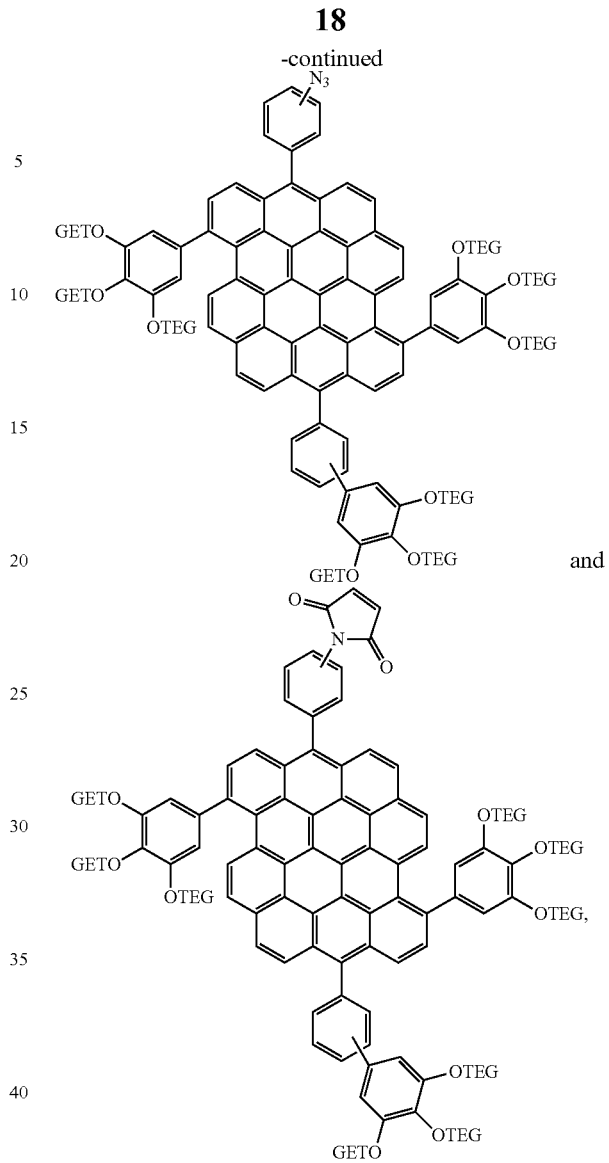

and in which Mes means a mesityl group and OTEG means a 3,4,5-tris(2,5,8,11-tetraoxatridecan-13-yloxy)phenyl group.

The DBOV compounds having the general formula (1) can be synthesized according to the reaction scheme shown in FIGS. 1 and 2 and as described below in the examples.

In accordance with a further aspect, the present invention relates to the use of the aforementioned compound having the general formula (1) for optical super-resolution microscopy, confocal microscopy (e.g. linear [single-photon] and/or nonlinear [multi-photon] imaging), wide field microscopy, fluorescence-lifetime imaging microscopy (FLIM), fluorescence resonance energy transfer (FRET) microscopy, FLIM-FRET microscopy, fluorescence anisotropy, fluorescence correlation spectroscopy (FCS), light-emitting devices.

For instance, the compound having the general formula (1) may be used in the optical high-resolution microscopy as fluorescent marker, wherein the high-resolution microscopy is photon tunneling microscopy (PTM), near-field optical random mapping (NORM) microscopy, structured illumination microscopy (SIM), spatially modulated illumination (SMI), ground state depletion (GSD), saturated structured illumination microscopy (SSIM), super-resolution optical fluctuation imaging (SOFI), omnipresent Localization Microscopy (OLM), stimulated emission depletion microscopy (STED) or single-molecule localization microscopy (SMLM), such as photoactivated localization microscopy (PALM), stochastic optical reconstruction microscopy (STORM), ground state depletion individual molecule return (GSDIM), binding activated localization microscopy (BALM) or fluorescence photo-activation localization microscopy (FPALM).

In accordance with still a further aspect, the present invention relates to the aforementioned compound for use in photothermal therapy. Subsequently, the present invention is further described by means of illustrative, but not limiting examples and figures.

EXAMPLE 1—(SYNTHESIS OF PEGYLATED 6,14-DIMESITYLDIBENZO[HI,ST]OVALENE)

(Synthesis of 6,6'-diiodo-[5,5'-bichrysene]-3,3'-dicarbaldehyde)

Figure 1:
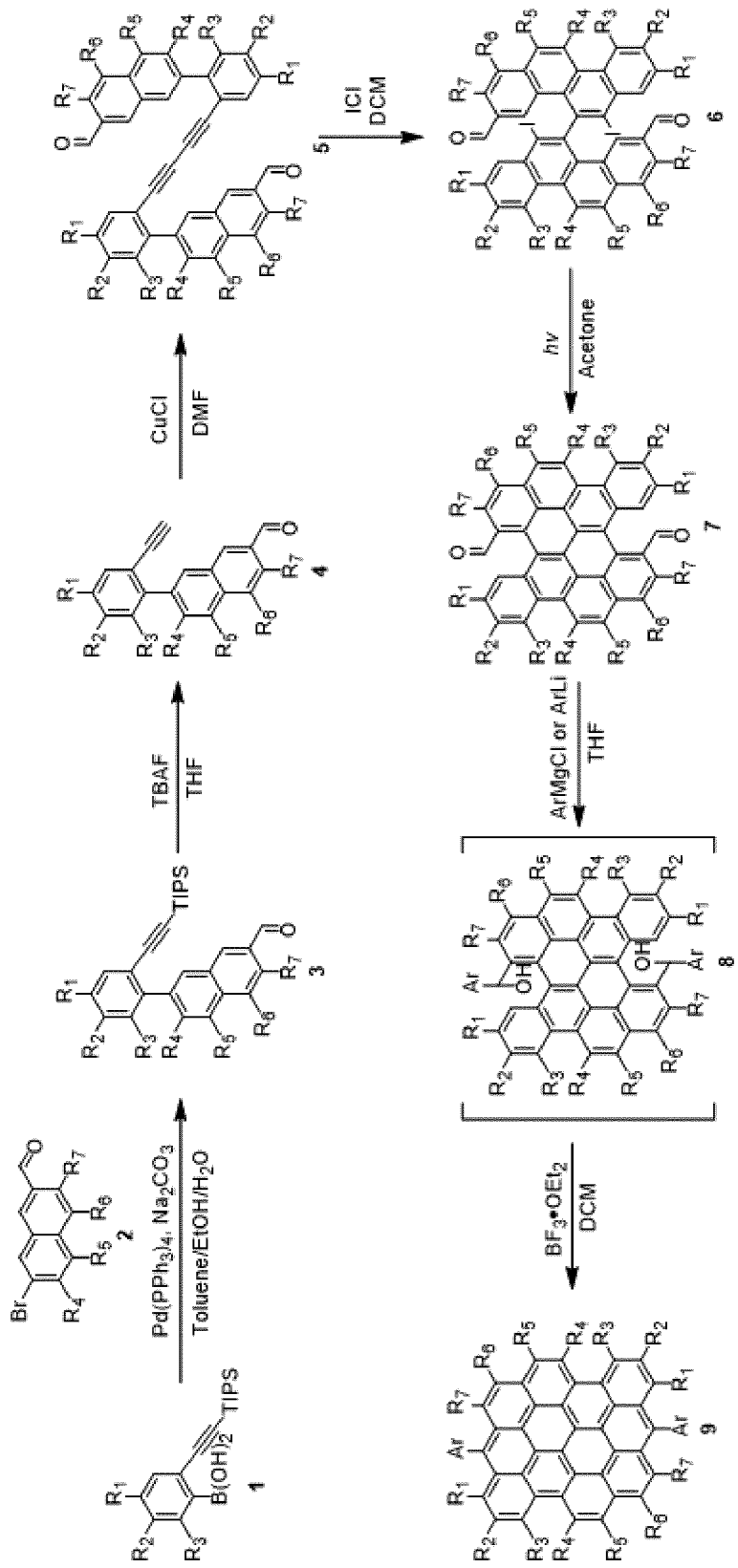
FIG. 1 shows a reaction scheme for synthesizing symmetric dibenzo[hi,st]ovalenes to be used in accordance with an embodiment of the present invention.
Figure 2:
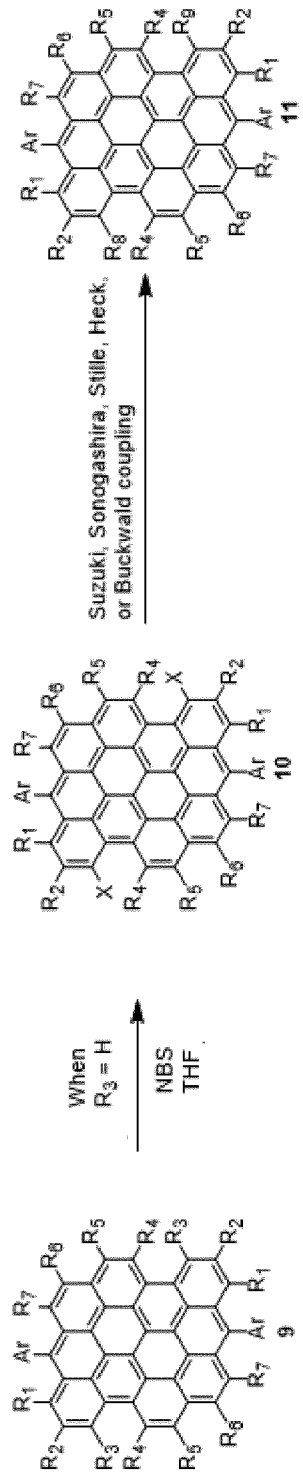
FIG. 2 shows a reaction scheme for converting a symmetric dibenzo[hi,st]ovalene into an asymmetric dibenzo[hi,st]ovalene to be used in accordance with another embodiment of the present invention.

In accordance with the reaction schemes shown in FIGS. 1 and 2, 6,6'-diiodo-[5,5'-bichrysene]-3,3'-dicarbaldehyde, which is compound 6 with all residues $R_1$ to $R_7$ being hydrogen atoms, was prepared starting from compound 5, in which all residues $R_1$ to $R_3$ are hydrogen atoms. The synthesis thereof is e.g. described in Nano Letters, 2017, volume 17, pages 5521-5525. More specifically, to a solution of compound 5 (2.0 g, 3.9 mmol) dissolved in anhydrous dichloromethane (240 mL) was added ICl (8.58 mmol, 8.58 mL, 1 M in dichloromethane). After stirring at room temperature for 2 hours, the excess ICl was quenched by addition of saturated aqueous $Na_2S_2O_3$ solution (50 mL). The organic phase was separated, washed with brine (50 mL), dried over $Na_2SO_4$ and evaporated. The residual solid was recrystallized with dichloromethane and methanol.

After filtration, the product (2.2 g, 76%) was obtained as white solid. The product had the following characteristics:

Mp: >400° C.; $^1$H NMR (300 MHz, Methylene Chloride-$d_2$) δ9.18 (d, J=9.2 Hz, 2H), 9.00 (d, J=8.5 Hz, 2H), 8.72 (s, 2H), 8.53-8.42 (m, 4H), 8.28 (d, J=9.1 Hz, 2H), 8.04 (d, J=8.3 Hz, 2H), 7.98-7.88 (m, 2H), 7.86-7.74 (m, 4H); $^{13}$C NMR (75 MHz, Methylene Chloride-$d_2$) δ191.8, 150.1, 137.4, 135.3, 134.6, 134.5, 133.7, 132.1, 130.9, 130.5, 130.4, 130.2, 129.7, 129.5, 129.3, 125.7, 124.4, 123.7, 114.1; FD-MS (8 kV): m/z 762.2; HRMS (MALDI-TOF): m/z Calcd for $C_{38}H_{20}I_2O_2$: 761.9553 [M]$^+$, found: 761.9553 (error=0 ppm).

Thus, it was shown that the product had the formula:

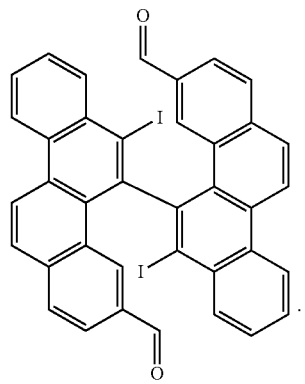 [SMILES: O=Cc1ccc2ccc3c4ccccc4c(I)c(-c4c(I)c5ccccc5c5ccc6ccc(C=O)cc6c45)c3c2c1]

(Synthesis of 5,14-diformylbenzo[a]dinaphtho[2,1,8-cde:1',2',3',4'-ghi]perylene)

In accordance with the reaction scheme shown in FIG. 1, 5,14-diformylbenzo[a]dinaphtho[2,1,8-cde:1',2',3',4'-ghi]perylene, which is compound 7 with all residues $R_1$ to $R_7$ being hydrogen atoms, was prepared starting from compound 6 prepared as described above. More specifically, to a 3 L cylindrical quartz reactor containing 6,6'-diiodo-[5,5'-bichrysene]-3,3'-dicarbaldehyde (300 mg, 0.394 mmol) was added a mixture of acetone (600 mL) and triethylamine (6 mL). Then the mixture was degassed by bubbling with Ar for 20 minutes. After that, the reaction mixture was stirred and irradiated at room temperature in a photoreactor equipped with six 300 nm wavelength UV lamps with strong stirring for 2 hours.

After cooling down to room temperature, the solvent was evaporated and the residue was purified by column chromatography (n-hexane:ethyl acetate=4:1) to give the product (170 mg, 86% yield) as red solid. The product had the following characteristics, which was further confirmed by X-ray single crystal structure analysis. Mp: >400° C.; $^1$H NMR (300 MHz, 1,1,2,2-tetrachloroethane-$d_2$) δ9.46 (s, 2H), 9.01 (d, J=9.1 Hz, 2H), 8.90 (d, J=8.4 Hz, 2H), 8.52-8.42 (m, 4H), 8.34 (t, J=9.1 Hz, 4H), 7.83-7.72 (m, 2H), 7.64 (dd, J=8.1, 1.1 Hz, 2H); $^{13}$C NMR (75 MHz, $C_2D_2Cl_4$) δ 190.8, 133.7, 131.7, 131.6, 130.6, 128.5, 128.2, 127.9, 127.5, 127.1, 127.1, 125.9, 124.9, 124.4, 124.0, 123.9, 123.2, 121.2, 120.6; FD-MS (8 kV): m/z 506.9; HR MS (MALDI-TOF): m/z Calcd for $C_{38}H_{18}O_2$: 506.1307 [M]$^+$, found: 506.1288 (error=−3.7 ppm).

Thus, it was shown that the product had the formula:

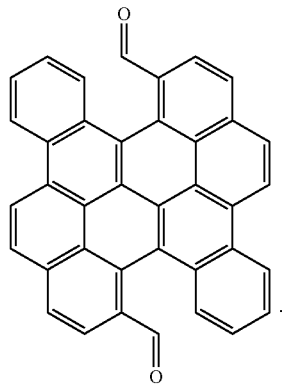 [SMILES: O=Cc1ccc2ccc3c4ccccc4c4c5c(C=O)ccc6ccc7c8ccccc8c8c1c2c3c4c8c7c65]

(Synthesis of 6,14-dimesityldibenzo[hi,st]ovalene)

To a solution of 5,14-diformylbenzo[a]dinaphtho[2,1,8-cde:1',2',3',4'-ghi]perylene (7) (5 mg, 10 μmol) in anhydrous THF (5 mL) was added mesitylmagnesium bromide (0.15 mL, 150 μmol, 1.0 M in ether) dropwise under the protection of Ar. The mixture was stirred at room temperature for 2 h. After completion of the reaction, the yellow green colored solution was poured into saturated aqueous solution of NH$_4$Cl (10 mL) and then extracted with ethyl acetate (20 mL) for 3 times. The combined organic layers were washed with brine (30 mL), dried over Na$_2$SO$_4$, and evaporated. After drying under vacuum using an oil pump for 2 h, the residue was redissolved in anhydrous dichloromethane (50 mL) and BF$_3$·OEt$_2$ (0.5 mL) was added using a syringe. The mixture was stirred at room temperature for 2 h. After completion of the reaction, the mixture was poured into saturated NaHCO$_3$ solution (10 mL). The organic phase was separated and dried over Na$_2$SO$_4$. The solvents were evaporated under reduced pressure and the residue was purified by column chromatography over silica gel (eluent: n-hexane/DCM=10: 1) to give 6,14-dimesityldibenzo[hi,st]ovalene (4 mg, 56%) as blue powder. TLC R$_f$=0.6 (n-hexane/ethyl acetate=10: 1).

The product had the following characteristics:

Mp: >400° C.; $^1$H NMR (700 MHz, o-dichlorobenzene-d$_4$) δ 9.33 (d, J=7.8 Hz, 2H), 9.04 (d, J=7.2 Hz, 2H), 8.44 (d, J=7.4 Hz, 2H), 8.00 (d, J=9.1 Hz, 2H), 7.98 (d, J=8.3 Hz, 2H), 7.89 (t, J=7.5 Hz, 2H), 7.78 (d, J=9.0 Hz, 2H), 7.19 (s, 4H), 2.50 (s, 6H), 1.99 (s, 12H); FD-MS (8 kV): m/z 709.5; HRMS (MALDI-TOF): m/z Calcd for C$_{56}$H$_{36}$: 708.2817 [M]$^+$, found: 708.2814.

Thus, it was shown that the product had the formula:

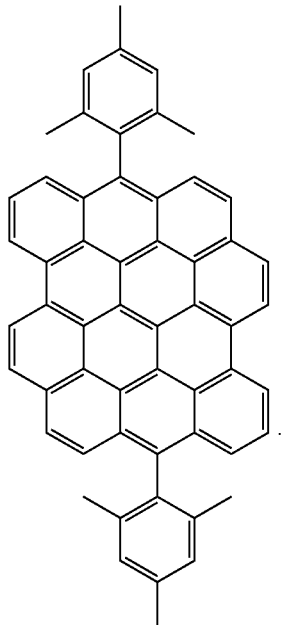 [SMILES: Cc1cc(C)c(-c2c3cccc4c5ccc6ccc7c(-c8c(C)cc(C)cc8C)c8cccc9c%10ccc%11ccc2c2c%11c%10c%10c(c89)c7c6c5c%10c2c34)c(C)c1]

(Synthesis of 3,11-dibromo-6,14-dimesityldibenzo[hi,st]ovalene)

To a solution of 6,14-dimesityldibenzo[hi,st]ovalene (14 mg, 0.020 mmol) dissolved in tetrahydrofuran (70 mL) was added N-bromosuccinimide (NBS) (14 mg, 0.079 mmol). The resulting mixture was stirred at room temperature for 2 h. The solvent was evaporated and the residue was purified by column chromatography to give the product (14 mg, 84%) as blue solid. The product had the following characteristics:

Mp: >400° C.; $^1$H NMR (700 MHz, THF-d$_8$) δ 10.67 (d, J=8.3 Hz, 2H), 8.72 (d, J=8.5 Hz, 2H), 8.34 (d, J=8.8 Hz, 2H), 8.29 (d, J=9.2 Hz, 2H), 7.87 (d, J=9.0 Hz, 2H), 7.85 (d, J=8.8 Hz, 2H), 7.27 (s, 4H), 1.93 (s, 12H); MS (MALDI-TOF): m/z Calcd for C$_{54}$H$_{30}$Br$_2$: 864.10 [M]$^+$, found: 864.06.

Thus, it was shown that the product had the formula:

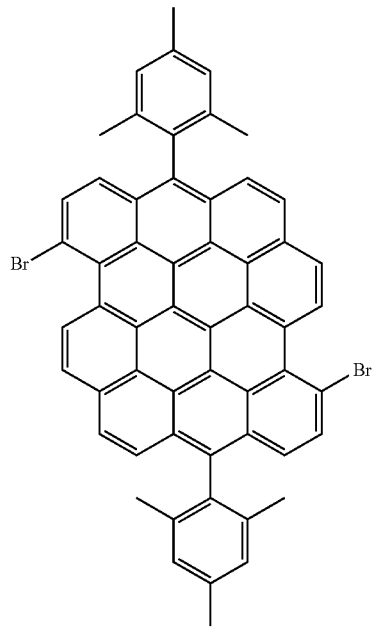 [SMILES: Cc1cc(C)c(-c2c3ccc(Br)c4c5ccc6ccc7c(-c8c(C)cc(C)cc8C)c8ccc(Br)c9c%10ccc%11ccc2c2c%11c%10c%10c(c89)c7c6c5c%10c2c34)c(C)c1]

(Synthesis of 3,4,5-tris(2,5,8,11-tetraoxatridecan-13-yloxy)phenyl substituted 6,14-dimesityldibenzo[hi,st]ovalene)

To a Schlenk tube equipped with a stirring bar was added dibrominated 6,14-dimesityldibenzo[hi,st]ovalene (3.0 mg, 3.5 μmol), 3,4,5-tris(2,5,8,11-tetraoxatridecan-13-yloxy)phenyl boronic acid pinacol ester (12 mg, 14 μmol), Pd(PPh$_3$)$_4$ (1.6 mg, 1.4 μmol) and K$_2$CO$_3$ (4.8 mg, 35 μmol). The reaction tube was evacuated and backfilled with Ar for three times before a mixture of toluene/EtOH/H$_2$O=2 mL/0.5 mL/0.5 mL was added. The mixture was degassed by three times freeze-pump-thaw cycles and heated at 90° C. overnight. After cooling down to room temperature, the reaction solution was extracted with ethyl acetate, washed with brine, dried over Na$_2$SO$_4$ and evaporated.

The residue was purified by column chromatography (ethyl acetate: MeOH=10:1 to 1:1) to give the product (5 mg, 69%) as blue oil. The product had the following characteristics:

$^1$H NMR (250 MHz, Deuterium Oxide) δ 8.95 (d, J=8.6 Hz, 1H), 8.24 (d, J=8.7 Hz, 1H), 8.09 (d, J=9.3 Hz, 1H), 7.95 (s, 2H), 7.73 (d, J=9.2 Hz, 1H), 7.26 (s, 2H), 7.01 (s, 2H), 4.31 (t, J=5.2 Hz, 2H), 3.93-3.84 (m, 2H), 3.75 (d, J=5.5 Hz, 8H), 3.68-3.31 (m, 84H), 3.27 (s, 8H), 3.19 (s, 6H), 1.96 (s, 6H). MS (MALDI-TOF): m/z Calcd for C$_{122}$H$_{152}$O$_{30}$: 2097.04 [M]$^+$, found: 2097.06

Thus, it was shown that the product had the formula:

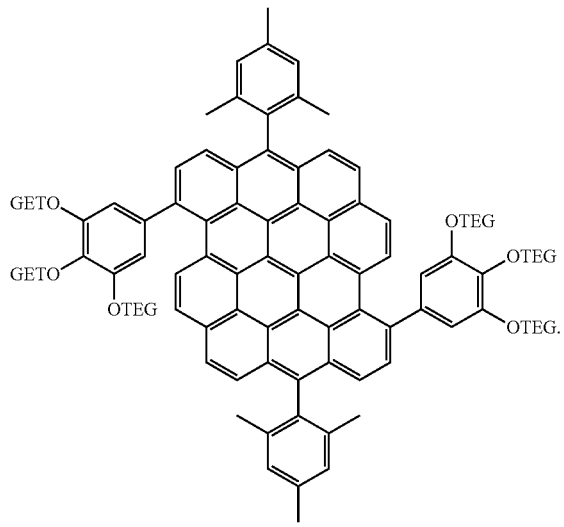

The solubility of this compound in water was evaluated at room temperature and was found to be 0.1 g/l.

Figure 3:
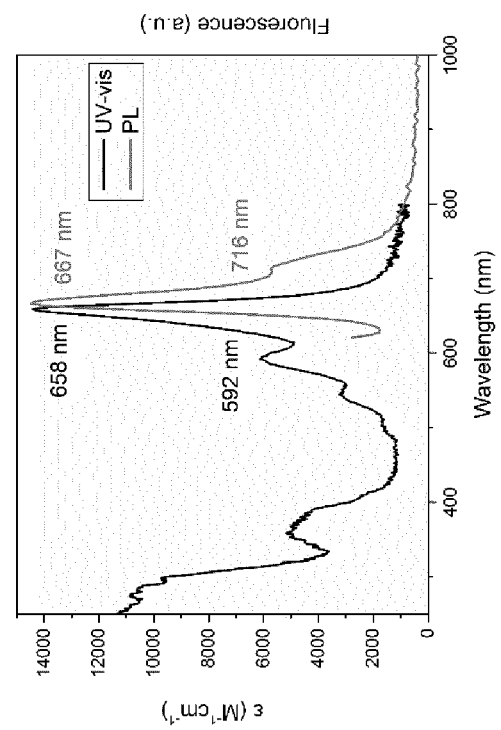
FIG. 3 show the absorption and emission spectra of the compound prepared in example 1 (Abs: absorbance; PI: PL-emission).

The absorption and emission spectra of this compound dissolved in water in a concentration of $10^{-6}$ mol/L are shown in FIG. 3 (UV-vis: absorbance; PI: PL-emission). The excitation wavelength for the PL measurement was 592 nm.

EXAMPLE 2—(EVALUATING THE WATER SOLUBLE COMPOUND SYNTHESIZED IN EXAMPLE 1 FOR CELL IMAGING)

3,4,5-tris(2,5,8,11-tetraoxatridecan-13-yloxy)phenyl substituted 6,14-dimesityldibenzo[hi,st]ovalene (subsequently abbreviated as DBOV-Mes-OTEG) synthesized in example 1 was evaluated concerning its properties.

Figure 4:
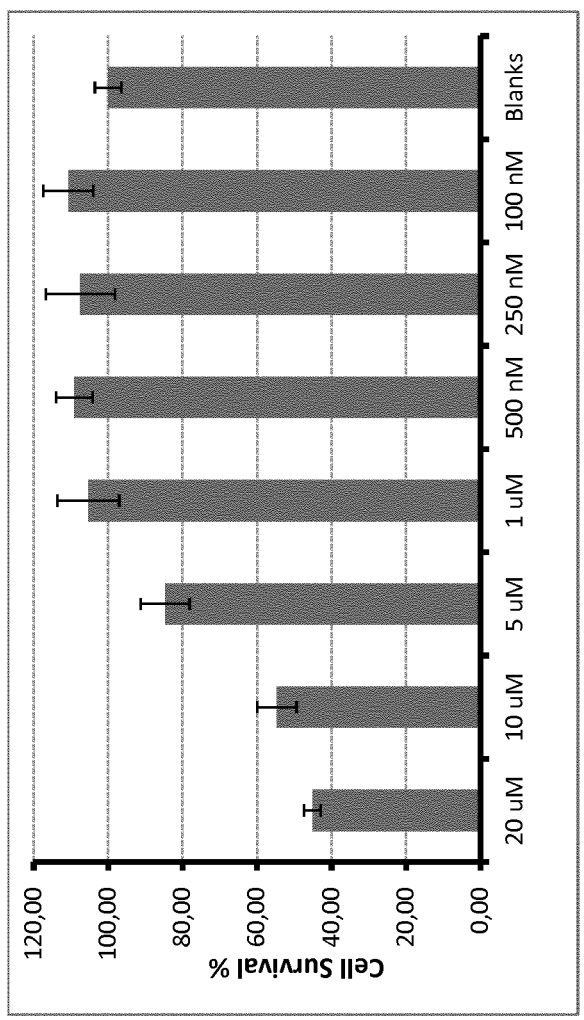
FIG. 4 shows the results of a cytotoxicity test DBOV-Mes-OTEG synthesized in example 1 in living cells.

More specifically, the cytotoxicity of DBOV-Mes-OTEG was tested in living cells. The results are shown in FIG. 4. The test showed that the water soluble DBOV-Mes-OTEG does not show any significant toxicity to cells in a concentration of 1 μM. Moreover, the uptake of DBOV-Mes-OTEG into living cells was investigated by imaging 21 hours with low laser intensity at the spinning disk confocal microscopy (Visitron). The test revealed that DBOV-Mes-OTEG was taken into the cytoplasm at the beginning of the incubation and that its location was after 21 hours incubation in the nucleus and nuclear membrane.

After the aforementioned live cell imaging, the samples were fixed and imaged in phosphate-buffered saline (PBS) without special imaging buffer. The test revealed that DBOV-Mes-OTEG was able to be imaged in the blinking mode under continuous exposure with high laser intensity 10 kW/cm² for 90 min. Furthermore, no significant decrease of blinking signals of DBOV-Mes-OTEG were detected. In addition, blinking signals could also be imaged with low laser intensity of 240 W/cm² and this reveals the possibility of living cell imaging with DBOV-Mes-OTEG.

The invention claimed is:

1. A compound having the general formula (1):

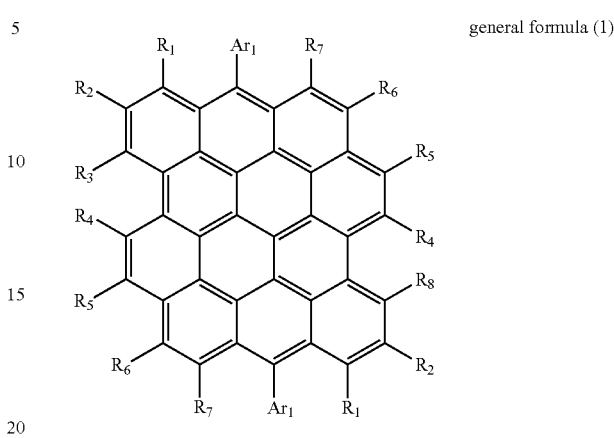

general formula (1)

wherein in the general formula (1) $R_1$ to $R_8$ and Ar are the same or different and are independently from each other selected from the group consisting of hydrogen, unsubstituted hydrocarbon groups, substituted hydrocarbon groups and inorganic groups, wherein at least one of $R_1$ to $R_8$ and Ar is a hydrophilic group.

2. The compound in accordance with claim 1, wherein in the general formula (1) at least one of $R_1$ to $R_8$ and Ar is a hydrophilic group, which is selected from the group consisting of anionic groups, cationic groups and non-charged groups comprising one or more groups selected from inorganic acid groups, organic acid groups, ester groups, amide groups, hydroxy groups, thiol groups, amino groups, aldehyde groups, ketone groups, acryl groups, ether groups, thioether groups and arbitrary combinations thereof.

3. The compound in accordance with claim 1, wherein in the general formula (1) at least one of $R_1$ to $R_8$ and Ar is a hydrophilic group, which is selected from the group consisting of quaternary amino groups, iminium salt groups, pyrrolidinium salt groups, pyrrolium salt groups, pyrazolidinum salt groups, pyrazolidinum salt groups, imidazolium salt groups, imidazolidinum salt groups, piperidinium salt groups, pyridinium salt groups, piperazinium salt groups, morpholinium salt groups, thiomorpholinium salt groups, oxazine salt groups, thiazine salt groups, indolinium salt groups, indole salt groups, sulfate groups, phosphate groups, nitrate groups, sulfonate groups, carboxylic acid groups, sulfonic acid groups, sulfenic acid groups, sulfinic acid groups, phosphonic acid groups, phosphenic acid groups, phosphinic acid groups, sugar groups, ester groups, amide groups, hydroxy groups, thiol groups, amino groups, aldehyde groups, ketone groups, acryl groups, ether groups, thioether groups, sulfhydryl groups, glycosidic linkages, peptide bonds, triazol groups and arbitrary combinations thereof.

4. The compound in accordance with claim 3, wherein in the general formula (1) at least one of $R_1$ to $R_8$ and Ar is a hydrophilic group, which is selected from the group consisting of quaternary amino groups, iminium salt groups, pyridinium salt groups, sulfate groups, sulfonate groups, carboxylic acid groups, sulfonic acid groups, ester groups, amide groups, ether groups, triazol groups and arbitrary combinations thereof.

5. The compound in accordance with claim 3, wherein in the general formula (1) at least one of $R_1$ to $R_8$ and Ar is a hydrophilic group, which is selected from polyalkylene glycol groups having a repeating number of 2 to 20 alkoxy units, groups comprising one to five polyalkylene glycol groups with each having a repeating number of 2 to 20 alkoxy units, sulfonate groups, quaternary ammonium groups, one or more amide groups, one or more imine groups and one or more pyridinium groups.

6. The compound in accordance with claim 3, wherein in the general formula (1) at least one of $R_1$ to $R_8$ and Ar is a phenyl group, which is substituted with two to five polyalkylene glycol groups.

7. The compound in accordance with claim 1, wherein in the general formula (1) at least two of $R_1$ to $R_8$ and Ar are a hydrophilic group.

8. The compound in accordance with claim 1, which has a solubility in water at 23° C. of at least 0.01 g/l.

9. The compound in accordance with claim 1, wherein in the general formula (1):
  $R_1$ is hydrogen or a $C_{1-20}$-alkyl group,
  $R_3$ and $R_8$ are a hydrophilic group,
  $R_2$ and $R_4$ to $R_7$ are hydrogen and
  Ar is aryl, a $C_{1-15}$-alkyl group or a trialkylsilyl alkynyl group.

10. The compound in accordance with claim 1, wherein in general formula (1) Ar is selected from the group consisting of phenyl, trifluorphenyl, 1,5-dimethylphenyl, mesitylene, triisopropylsilyl ethynyl, trimethylsilyl ethynyl, phenylsilyl ethynyl and $C_{1-15}$-alkyl groups.

11. The compound in accordance with claim 1, wherein in the general formula (1) at least one of $R_1$ to $R_8$ and Ar is a group with a terminal alkyne group.

12. A method comprising coupling the compound of claim 1 with a target molecule and performing optical super-resolution microscopy, confocal microscopy, wide field microscopy, fluorescence-lifetime imaging microscopy (FLIM), fluorescence resonance energy transfer (FRET) microscopy, FLIM-FRET microscopy, fluorescence anisotropy or fluorescence correlation spectroscopy (FCS).

13. A method comprising coupling the compound of claim 1 with a target molecule and performing photon tunneling microscopy (PTM), near-field optical random mapping (NORM) microscopy, structured illumination microscopy (SIM), spatially modulated illumination (SMI), ground state depletion (GSD), saturated structured illumination microscopy (SSIM), super-resolution optical fluctuation imaging (SOFI), omnipresent Localization Microscopy (OLM), stimulated emission depletion microscopy (STED) single-molecule localization microscopy (SMLM), photoactivated localization microscopy (PALM), stochastic optical reconstruction microscopy (STORM), ground state depletion individual molecule return (GSDIM), binding activated localization microscopy (BALM) or fluorescence photo-activation localization microscopy (FPALM).

\* \* \* \* \*